(12) United States Patent
Ko

(10) Patent No.: US 8,476,238 B2
(45) Date of Patent: Jul. 2, 2013

(54) **USES OF AN IMMUNOMODULATORY PROTEIN (GMI) FROM *GANODERMA MICROSPORUM***

(75) Inventor: Jiunn-Liang Ko, Taichung Hsien (TW)

(73) Assignee: Mycomagic Biotechnology Co., Ltd., Taipei County (TW)

( * ) Notice: Subject to any disclaimer, the term of this patent is extended or adjusted under 35 U.S.C. 154(b) by 127 days.

(21) Appl. No.: 12/826,230

(22) Filed: Jun. 29, 2010

(65) Prior Publication Data
US 2011/0318429 A1 Dec. 29, 2011

(51) Int. Cl.
*A61K 38/00* (2006.01)
*A61K 33/24* (2006.01)
*A61P 35/04* (2006.01)

(52) U.S. Cl.
USPC .......................................... 514/19.8; 424/649

(58) Field of Classification Search
None
See application file for complete search history.

(56) References Cited

U.S. PATENT DOCUMENTS

| | | | |
|---|---|---|---|
| 5,334,704 A * | 8/1994 | Tsunoo et al. | 530/371 |
| 5,844,001 A * | 12/1998 | McClay et al. | 514/648 |
| 7,601,808 B2 * | 10/2009 | Lin | 530/350 |
| 2007/0207954 A1 * | 9/2007 | Lin | 514/12 |

OTHER PUBLICATIONS

Van Horssen et al. TNF-alpha in Cancer Treatment: Molecular Insights, Antitumor Effects, and Clinical Utility. The Oncologist. 2006, vol. 11, pp. 297-408.*

Tzyy-Rong Jinn et al., Functional Expression of FIP-gts, a Fungal Immunomodulatory Protein from *Ganoderma tsugae* in Sf21 Insect Cells, Biosci. Biotechnol. Biochem., 2006, pp. 2627-2634, vol. 70, Issue 11.

Hao-Chi Hsu et al., Fip-vvo, a New Fungal Immunomodulatory Protein Isolated From *Volvariella volvacea*, Biochem J., 1997, pp. 557-565, vol. 323.

Chien-Huang Liao et al., Induction of Premature Senescence in Human Lung Cancer by Fungal Immunomodulatory Protein from *Ganoderma tsugae*, Food and Chemical Toxicology, 2008, pp. 1851-1859, vol. 46.

Chien-Huang Liao et al., Transcriptionally Mediated Inhibition of Telomerase of Fungal Immunomodulatory Protein from *Ganoderma tsugae* in A549 Human Lung Adenocarcinoma Cell Line, Molecular Carcinogenesis, 2006, pp. 220-229, vol. 45.

Jiunn-Liang Ko et al., A New Fungal Immunomodulatory Protein, FIP-fve Isolated from the Edible Mushroom, *Flammulina velutipes* and Its Complete Amino Acid Sequence, Eur. J. Biochem, 1995, pp. 244-249, vol. 228.

Ching-Hsiung Lin et al., A New Immunomodulatory Protein from *Ganoderma microsporum* Inhibits Epidermal Growth Factor Mediated Migration and Invasion in A549 LUng Cancer Cells, Process Biochemistry, 2010.

* cited by examiner

*Primary Examiner* — Marcela M Cordero Garcia
(74) *Attorney, Agent, or Firm* — WPAT, P.C.; Anthony King

(57) ABSTRACT

The invention provides a method for inhibiting EGF receptor activity comprising contacting an EGF receptor with an immunomodulatory protein (GMI) from *Ganoderma microsporum*, or a recombinant thereof. Also provided is a method for treating invasion and metastasis of cancer cells, comprising administering an effective amount of an immunomodulatory protein (GMI) from *Ganoderma microsporum*, or a recombinant thereof, to a subject in need of such treatment.

10 Claims, 11 Drawing Sheets
(3 of 11 Drawing Sheet(s) Filed in Color)

USES OF AN IMMUNOMODULATORY PROTEIN (GMI) FROM *GANODERMA MICROSPORUM*

FIELD OF THE INVENTION

The present invention relates to the new uses of an immunomodulatory protein (GMI) from *Ganoderma microsporum*, a combination therapy of GMI and an anti-cancer agent and a pharmaceutical composition comprising GMI and an anti-cancer agent. In particular, GMI can be used to inhibit EGF receptor activity, treat invasion and metastasis of cancer cells, and promote wound healing.

BACKGROUND OF THE INVENTION

Neovascularization is critical for the growth for tumors and is important in a variety of angiogenic diseases, such as diabetic retinopathy, arthritis, psoriasis and haemangiomas. More than 70% of cancer patients die from metastatic dissemination of the initial tumor. Tumor neovascularization is the crucial process for survival of a primary tumor and for metastatic dissemination. Angiostatic steroids and heparin with anti-angiogenic agents such as protamin have been used as therapies to suppress tumor growth. These therapeutic approaches have serious limitations, because when the dose of heparin exceeds an optimum level for inhibition of angiogenesis, both tumor growth and angiogenesis are stimulated. Also, high doses of cortisone that are required for antiangiogenesis leads to immunosuppression. Acquisition of an angiogenic phenotype marked a transition from hyperplasia to neoplasia.

Growth factors are substances that induce cell proliferation, typically by binding to specific receptors on cell surfaces. One such growth factor is epidermal growth factor (EGF). EGF induces proliferation of a variety of cells in vivo, and is required for the growth of most cultured cells. EGF is a single-chain polypeptide having a molecular weight of 6 Kd (53 amino acid residues) and three internal disulfide bonds. These three well characterized internal disulfide bonds of the epidermal growth factor peptide define three "loops," the A, B and C loops. Generally, the A loop is characterized between amino acid residues 1-19, the B loop is characterized between residues 20-31, and the C loop is characterized between residues 34-43. EGF is also known to be a powerful stimulator of cell proliferation. In particular, EGF has been shown to stimulate the growth of epithelial cell tissue in a variety of preparations. Epithelial growth factor receptor (EGFR) plays an important role in epithelial biology and in many human malignancies. EGFR is related to the viral oncogeny, v-erb B, and is overexpressed in many human tumors, including brain, bladder, breast, and squamous cell carcinomas of the head, neck and lung. Thus, EGF-R "activation" is an important regulatory event in stimulating the division of many normal cells as well as in the aberrant growth of some tumor cells. Complete EGF peptides, and antibodies which mimic their action, have been used in such diverse processes as screening for tumoricidal activity and promotion of wound healing. EGFR is a member of the receptor family comprising four, highly homologous proteins, HER2, HER3, and HER4 as well as EGFR. Those proteins in this family consist of an extracellular domain, a transmembrane domain, and an intracellular tyrosine kinase domain. Binding of the ligand such as epithelial growth factor (EGF) activates the intracellular tyrosine kinase domain to induce autophosphorylation of the receptor, which initiates the signaling cascade involved in cell proliferation and survival. EGFR is one of the most suitable targets in cancer therapy.

Lung cancer is the most common malignancy among men and women, and remains the leading cause of cancer-related deaths. Non-small lung carcinoma (NSCLC) accounts for approximately 75-85% of lung cancers. Conventional lung cancer treatments generally show poor clinical response, thus it is of utmost importance to develop novel treatment strategies directed against metastasis. EGFR overexpression occurs in 40-80% of NSCLCs. The EGFR pathway contributes to the pathogenesis and progression of human carcinoma, including cell proliferation, apoptosis, angiogenesis and metastatic spread. Notably, EGFR-directed tyrosine kinase inhibitors (TKIs) such as gefitinib (Iressa, ZD1839), lapatinib (Tykerb, GW572016) and erlotinib (Tarceva, OSI-774) have different sensitivities based on the specific subtypes of NSCLC patients. In addition, gefitinib has been used as a single agent in NSCLC with modest efficacy. However, patients respond differently to this agent, and very recently these responses have been correlated with the presence of activating mutations in the tyrosine kinase domain of EGFR. EGF interacts with EGFR, leading to receptor dimerization, activation of its kinase activity and autophosphorylation of EGFR on tyrosine residues. EGF is also associated with the growth and invasion of various malignant tumors via different pathways. Several studies have shown that EGF is frequently elevated in lung cancer, and up-regulation of EGF has been shown to be related to disease progression and poor prognosis (Gorgoulis et al., 1992, *Anticancer Res*, 12, 1183-1187). This suggests that EGF plays a major role in lung tumorigenesis. Therefore, the EGF/EGFR interaction may be important for the development of lung cancer.

Herbal therapies have increasingly been considered viable alternative treatments for cancers. Lingzhi (a species of *Basidiomycetes*) is an herbal mushroom, used in traditional Chinese medicine for at least 2,000 years. Many therapeutic effects have been reported of Lingzhi species, such as immunomodulatory, anti-tumor, hepato-protective, antioxidant, and cholesterol-lowering effects (Jinn et al., 2006, *Biosci Biotechnol Biochem*, 70, 2627-2634). All of these therapeutic effects are attributed to triterpenoids, polyssacharides, and glycoproteins (Boh et al., 2007, *Biotechnol Annu Rev*, 13, 265-301; Jinn et al., 2006, *Biosci Biotechnol Biochem*, 70, 2627-2634). A new glycoprotein class in Lingzhi named fungal immunomodulatory proteins (FIPs) was recently identified. So far, at least 4 FIPs have been isolated and purified from *Ganoderma lucidum*, LZ-8, (*G. lucidum*), including FIP-fve (*Flammulina veltipes*), FIP-vvo (*Volvariella volvacea*), FIP-gts (*Ganoderma tsugae*), and FIP-gja (*Ganoderma sinensis*) (Hsu et al., 1997, *Biochem J*, 323 (Pt 2), 557-565; Ko et al., 1995, *Eur J Biochem*, 228, 244-249; Xuanwei et al., 2008, *Planta Med*, 74, 197-200). According to a previous study, FIP-gts from *G. tsugae*, a popular chemopreventive mushroom in Asia, has anti-cancer function and is involved in the regulation of hTERT/telomerase expression (Liao et al., 2006, *Mol Carcinog*, 45, 220-229). In addition, FIP-gts inhibits the growth of A549 cancer cells, leading to cell cycle arrest, consequently inducing premature cellular senescence in lung cancer cells. Moreover, FIP-gts results in significant inhibition of tumor growth in athymic nude mice implanted with A549 cells (Liao et al., 2008, *Food Chem Toxicol*, 46, 1851-1859). US 20100009915 provides a method for suppressing proliferation of a cancer cell and a method for suppressing a tumor cell mobility, comprising providing to the tumor cell a purified polypeptide of a fungal immunomodulatory protein, LZ-8.

U.S. Pat. No. 7,601,808 discloses an immunomodulatory protein (GMI) cloned from *Ganoderma microsporum* and this protein has immunomodulator efficiency. However, since GMI is a newly found immunomodulatory protein and its anti-cancer effects have not been investigated, there is still a need in the art to investigate its anticancer applications.

SUMMARY OF THE INVENTION

One object of the invention is to provide a method for inhibiting EGF receptor activity comprising contacting an EGF receptor with an immunomodulatory protein (GMI) from *Ganoderma microsporum*, or a recombinant thereof.

Another object of the invention is to provide a method for treating invasion and metastasis of cancer cells, comprising administering an effective amount of an immunomodulatory protein (GMI) from *Ganoderma microsporum*, or a recombinant thereof, to a subject in need of such treatment.

A further object of the invention is to provide a pharmaceutical composition, comprising GMI a recombinant thereof and an-anti cancer agent.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1, 1A:
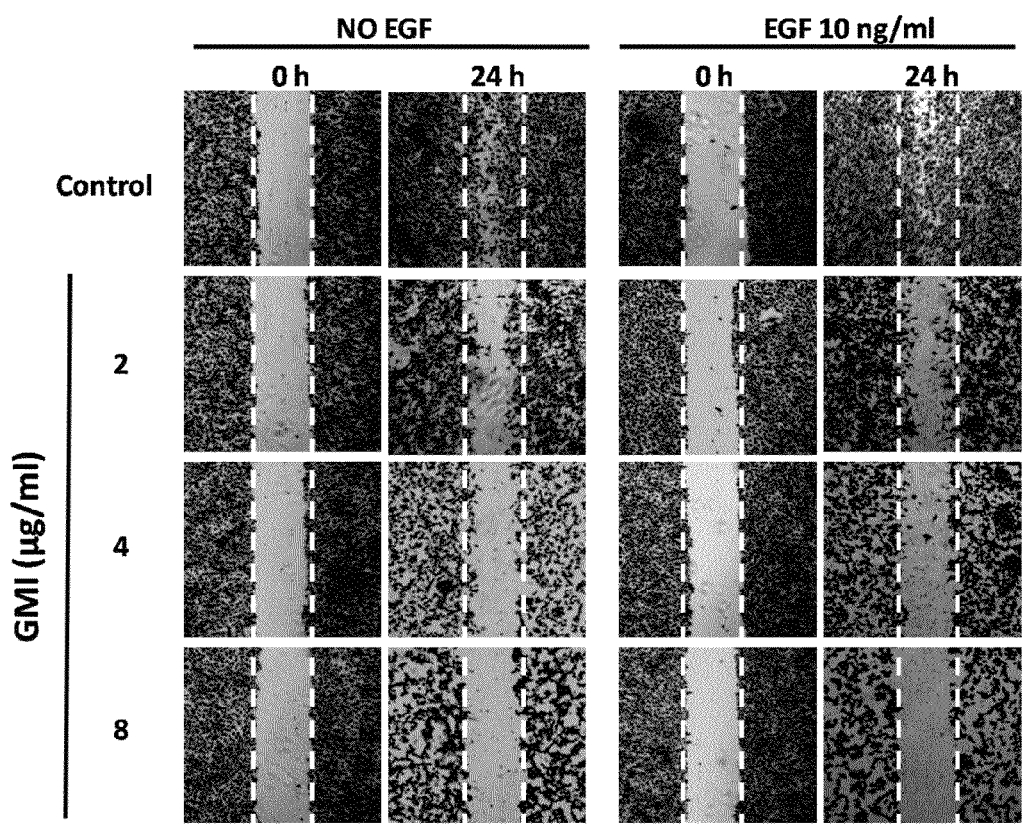
FIG. 1 shows the inhibition of GMI and AG1478 in cancer cell migration in A549 cells. A549 cells ($1.2 \times 10^5$ cells/24 well) were treated with increasing doses of GMI (2, 4, 8 µg/ml) for 24 h. Wound-healing assay was carried out to evaluate the inhibitory effects of (A) GMI or (B) AG1478 on A549 cell migration. Confluent monolayers of A549 cells were scarred, and repair was monitored microscopically after 24 h of treatment with (A) GMI or (B) AG1478. The cells migrating into the wound area were counted on the basis of the dashed line as time zero.
Figure 1:
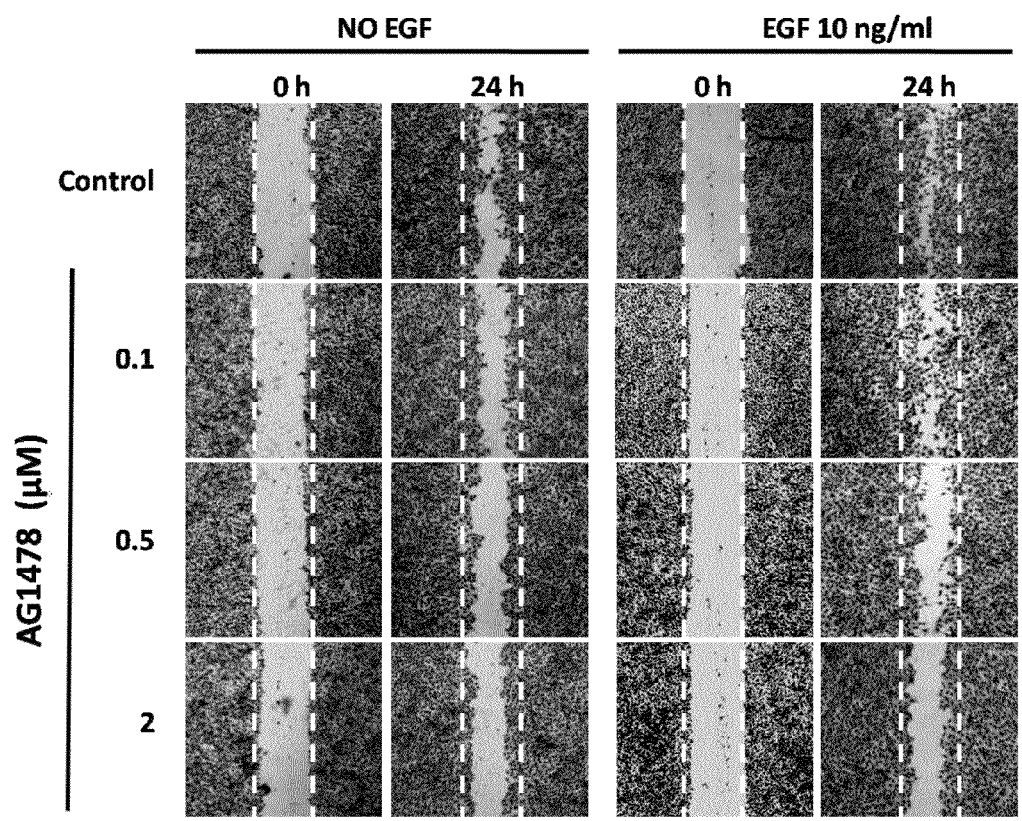

The present invention is based on the discovery that an immunomodulatory protein (GMI) from *Ganoderma microsporum* is effective in inhibiting EGF receptor activity and treating invasion and metastasis of cancer cells. Particularly, the GMI inhibits EGF-induced invasive growth of cancer cells, including migration and invasion, through blocking of the EGF/phosphoEGFR-PI3K/Akt pathway. GMI induces a dose-dependent decrease in invasion with increasing concentrations of GMI. The invention also found significant changes in actin following GMI repression of EGF-induced activation of EGF/phosphoEGFR-PI3K/Akt pathway, so GMI can be used as a strong actin deploymerizer in tumor cells. These findings suggest that GMI has considerable potential for cancer chemoprevention. In particular, GMI in combination with an anti-cancer drug(s) provides advantageous effect (preferably synergistic effect) in the treatment and/or prevention of cancer or in the inhibition of metastasis or invasion.

In one aspect, the invention provides a method for inhibiting EGF receptor activity comprising contacting an EGF receptor with an immunomodulatory protein (GMI) from *Ganoderma microsporum*, or a recombinant thereof.

In another aspect, the present invention provides a method for inhibiting and/or treating invasion and metastasis of cancer, comprising administering an effective amount of an immunomodulatory protein (GMI) from *Ganoderma microsporum*, or a recombinant thereof, to a subject in need of such treatment. In one embodiment, the treatment of invasion and metastasis is through blocking of the EGF/phospho-EGFR-PI3K/Akt pathway.

In a further aspect, the present invention provides a method for inhibiting and/or treating cancer and/or invasion and metastasis of cancer, comprising administering GMI or a recombination thereof and an anti-cancer agent simultaneously, sequentially or separately. In another further aspect, the present invention provides a pharmaceutical composition, comprising GMI a recombinant thereof and an-anti cancer agent.

In another aspect, the present invention provides a pharmaceutical composition, comprising GMI a recombinant thereof and an-anti cancer agent. Preferably, the composition exhibits a synergist effect in treating and/or preventing cancer.

According to the invention, the immunomodulatory protein (GMI) is from *Ganoderma microsporum* or a recombinant thereof. More preferably, the GMI has the amino acid sequences: (1) -Leu-Ala-Trp-Asn-Val-Lys-(LAWNVK; SEQ ID NO:1) and (2)-Asp-Leu-Gly-Val-Arg-Pro-Ser-Tyr-Ala-Val-(DLGVRPSYAV; SEQ ID NO:2) or the amino acid sequence of:

(SEQ ID NO: 3)
MSDTALIFTLAWNVKQLAFDYTPNWGRGRPSSFIDTVTFPTVLTDKAY

TYRVVVSGKDLGVRPSYAVESDGSQKINFLEYNSGYGIADTNTIQVYV

IDPDTGNNFIVAQWN.

According to the invention, the terms "treatment," "treating" and the like are used herein to generally mean obtaining a desired pharmacologic, physiologic or cosmetic effect. The effect may be prophylactic in terms of completely or partially preventing a condition, appearance, disease or symptom and/or may be therapeutic in terms of a partial or complete cure for a condition and/or adverse effect attributable to a condition or disease. "Treatment" as used herein covers any treatment of a condition, disease or undesirable appearance in a mammal, particularly a human, and includes: (a) preventing the disease (e.g. cancer), condition (pain) or appearance (e.g. visible tumors) from occurring in a subject which may be predisposed to it but has not yet been observed or diagnosed as having it; (b) inhibiting the disease, condition or appearance, i.e., causing regression of condition or appearance; (c) relieving the disease, condition or appearance, i.e., causing regression of a condition or appearance.

The term "inhibit" as used herein with reference to cancer invasion and metastasis refers to any reduction in cancer invasion and metastasis by GMI or pharmaceutical composition of the invention.

The term "effective amount" is the quantity of compound which achieves a beneficial clinical outcome when the compound is administered to a subject. For example, when a compound of the invention is administered to a subject with a cancer, a "beneficial clinical outcome" includes reduction in tumor mass, reduction in metastasis, reduction in the severity of the symptoms associated with the cancer and/or increase in the longevity of the subject.

According to the invention, the term "metastasis" or "invasion" refers to the ability of a cell to migrate through a physiological barrier or to protease components of an extracellular matrix. Preferred physiological barriers include basement membranes and other extracellular matrices which are well known in the art. Cell invasion is correlated to the secretion or excretion of proteolytic enzymes from a cell. Preferred proteolytic enzymes include MMPs.

In one embodiment, the invasion and metastasis of cancer cells is epidermal growth factor mediated migration and invasion of cancer cells. Epidermal growth factor (EGF) is a small molecule which exhibits homology with regions of the TGF-alpha molecule. It is produced by macrophages and epidermal cells with the keratinocyte and fibroblast as targets. Its primary role is to stimulate keratinocytes to migrate across a wound's provisional matrix and induce epidermal regeneration. EGF, like all growth factors, binds to specific high-affinity, low-capacity receptors on the surface of responsive cells. Intrinsic to the EGF receptor is tyrosine kinase activity, which is activated in response to EGF binding. The kinase domain of the EGF receptor phosphorylates the EGF receptor itself (autophosphorylation) as well as other proteins, in signal transduction cascades, that are associated with the receptor following activation. The activation of EGFR is highly involved in the processes of tumor proliferation and progression, including cell proliferation, inhibition of apoptosis, angiogenesis and metastasis. EGFR shows relatively high expression in epithelial cancers and the expression correlates with tumor progression, and therefore it is one of the most suitable targets in cancer therapy.

Preferably, the cancer is lung cancer (more preferably, non-small lung carcinoma, NSCLC), squamous cell carcinomas of the lung, head and neck, breast cancer, ovarian cancer, prostate cancer, gastric carcinoma, cervical cancer, esophageal carcinoma, bladder cancer, brain cancer, liver cancer, or colon cancer.

In another embodiment, as a therapeutic agent to promote wound healing, GMI may be used in a topical treatment form to be applied externally on any compromised skin condition. For such uses, it is contemplated that GMI includes a carrier in a coupled form. By way of example, compromised skin conditions include external skin injuries such as burns, rashes, abrasions, and the like. Use of GMI as a treatment to promote wound healing is contemplated to be particularly suitable in the treatment of burns.

GMI can be administered to a patient either alone or in pharmaceutical compositions where it is mixed with suitable carriers and excipients. GMI can be administered parenterally, such as by intravenous injection or infusion, intraperitoneal injection, subcutaneous injection, or intramuscular injection. GMI can be administered orally or rectally through appropriate formulation with carriers and excipients to form tablets, pills, capsules, liquids, gels, syrups, slurries, suspensions and the like. GMI can be administered topically, such as by skin patch. GMI can be formulated into topical creams, skin or mucosal patch, liquids or gels suitable to topical application to skin or mucosal membrane surfaces. GMI can be administered by inhaler to the respiratory tract for local or systemic treatment of cancers. In one embodiment, the amount of GMI for administration may ranges from 250 µg to 500 µg for a human with 60 kg.

The dosage of GMI suitable for use according to the present invention can be determined by those skilled in the art on the basis of the disclosure herein. The medicament will contain an effective dosage (depending upon the route of administration and pharmacokinetics of the active agent) of GMI and suitable pharmaceutical carriers and excipients which are suitable for the particular route of administration of the formulation (i.e., oral, parenteral, topical or by inhalation). GMI is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

In one embodiment, GMI can be used in combination with radiotherapy and chemotherapy.

In another embodiment, the GMI a recombinant thereof can be combined with an anti-cancer agent for combination therapy in cancer and/or cancer invasion and metastasis. CMI a recombinant thereof also can be combined with an anti-cancer agent as a pharmaceutical composition. That is, the invention provides a pharmaceutical composition comprising GMI a recombinant thereof and an anti-cancer agent and the composition can treat and/or prevent cancer or treat and/or prevent cancer metastasis or invasion. Preferably, the cancer is lung cancer (more preferably, non-small lung carcinoma, NSCLC), squamous cell carcinomas of the lung, head and neck, breast cancer, ovarian cancer, prostate cancer, gastric carcinoma, cervical cancer, esophageal carcinoma, bladder cancer, brain cancer, liver cancer, or colon cancer. Particularly, the composition preferably exhibits a synergistic efficacy. According to the invention, the anti-cancer agent include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cisplatin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypernycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithineklerriene; emitefur; epirubicin; episteride; erlotinib; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunoruriicin hydrochloride; forfenimex; formestane; fostriecin; fotemustine; gadolinium texaphyrin; gallium nitrate; galocitabine; ganirelix; gefitinib; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; lapatinib; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+niyobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2, proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; rarnosetran; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonerrnin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium;

tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

According to the invention, the anti-cancer agent can be a therapeutic antibody, including but not limiting to HERCEPTIN® (Trastuzumab) (Genentech, Calif.), which is a humanized anti-HER2 monoclonal antibody for the treatment of patients with metastatic breast cancer; REOPRO® (abciximab) (Centocor), which is an anti-glycoprotein IIb/IIIa receptor on the platelets for the prevention of clot formation; ZENAPAX® (daclizumab) (Roche Pharmaceuticals, Switzerland), which is an immunosuppressive, humanized anti-CD25 monoclonal antibody for the prevention of acute renal allograft rejection; PANOREX®, which is a murine anti-17-IA cell surface antigen IgG2a antibody (Glaxo Wellcome/Centocor); BEC2, which is a murine anti-idiotype (GD3 epitope) IgG antibody (ImClone System); IMC-C225, which is a chimeric anti-EGFR IgG antibody (ImClone System); VITAXIN®, which is a humanized anti-.alpha.V.beta.3 integrin antibody (Applied Molecular Evolution/MedImmune); Campath 1H/LDP-03 which is a humanized anti CD52 IgG1 antibody (Leukosite); Smart M195, which is a humanized anti-CD33 IgG antibody (Protein Design Lab/Kanebo); RITUXAN®, which is a chimeric anti-CD20 IgG1 antibody (IDEC Pharm/Genentech, Roche/Zettyaku); LYMPHOCIDE®, which is a humanized anti-CD22 IgG antibody (Immunomedics); LYMPHOCIDE® Y-90 (Immunomedics); Lymphoscan (Tc-99m-labeled; radioimaging; Immunomedics); Nuvion (against CD3; Protein Design Labs); CM3, which is a humanized anti-ICAM3 antibody (ICOS Pharm); IDEC-114, which is a primated anti-CD80 antibody (IDEC Pharm/Mitsubishi); ZEVALIN®, which is a radiolabelled murine anti-CD20 antibody (IDEC/Schering AG); IDEC-131, which is a humanized anti-CD40L antibody (IDEC/Eisai); IDEC-151, which is a primatized anti-CD4 antibody (IDEC); IDEC-152, which is a primatized anti-CD23 antibody (IDEC/Seikagaku); SMART anti-CD3, which is a humanized anti-CD3 IgG (Protein Design Lab); 5G1.1, which is a humanized anti-complement factor 5 (C5) antibody (Alexion Pharm); D2E7, which is a humanized anti-TNF-alpha antibody (CAT/BASF); CDP870, which is a humanized anti-TNF-alpha Fab fragment (Celltech); IDEC-151, which is a primatized anti-CD4 IgG1 antibody (IDEC Pharm/SmithKline Beecham); MDX-CD4, which is a human anti-CD4 IgG antibody (Medarex(Eisai/Genmab); CD20-sreptdavidin (+biotin-yttrium 90; NeoRx); CDP571, which is a humanized anti-TNF-alpha IgG4 antibody (Celltech); LDP-02, which is a humanized anti-alpha-4-beta-7 antibody (LeukoSite/Genentech); OrthoClone OKT4A, which is a humanized anti-CD4 IgG antibody (Ortho Biotech); ANTOVA®, which is a humanized anti-CD40L IgG antibody (Biogen); ANTEGREN®, which is a humanized anti-VLA-4 IgG antibody (Elan); and CAT-152, which is a human anti-TGF-beta 2 antibody (Cambridge Ab Tech).

In a further embodiment, the anti-cancer agent can be selected from the group consisting of cisplatin, gefitinib, lapatinib and erlotinib.

The present invention evaluates the inhibitory effect of GMI on invasion and metastasis of cancer cells (especially, EGF-induced invasion and metastasis of cancer cells) and investigates the molecular mechanism involved. The present invention demonstrates that EGF treatment leads to PI3K/Akt increase, which results in upregulation of Rac1/Cdc42 activity and assembly of cell-cell contacts, as well as enhanced invasion by tumor cells. GMI inhibits EGF-induced A549 cell migration and invasion involving both PI3K/Akt and Stat3 pathways. Furthermore, GMI can inhibit the TNF-alpha induced MMP9 protease activity.

Without further elaboration, it is believed that one skilled in the art can utilize the present invention to its fullest extent on the basis of the preceding description. The following examples are, therefore, to be construed as merely illustrative and not a limitation of the scope of the present invention in any way.

EXAMPLE

Example 1

GMI Inhibits EGF-Induced Migration and Invasion in A549 Cells

Recombinant human EGF was purchased from Peprotech Inc. AG1478 was obtained from Calbiochem. Antibodies used for Western blotting against Phospho-specific EGFR Y1068 (ab40815) and cdc42 (ab41429) were obtained from ABCAM. Anti-phospho STAT3 Y705 (#9131), anti-phospho GSK-3β (#9336) and anti-phospho Akt Ser473 (#9271) were purchased from Cell Signaling. Other antibodies included monoclonal anti-β actin antibody (SIGMA) and Rac1 antibody (Upstate). GMI manufactured by Mycomagic Biotechnology Co., Ltd., was generated and ameliorated from *Ganoderma microsporum*.

The human lung carcinoma cell line, A549 [American Type Culture Collection (ATCC); CCL-185], was obtained from ATCC. The cells were grown in DMEM (Life Technologies) supplemented with 10% heat-inactivated fetal bovine serum (FBS; Life Technologies), as well as penicillin and streptomycin (100 mg/mL each), at 37° C. in a humidified atmosphere of 5% $CO_2$.

Expression of EGFR in small cell lung cancer cells has been previously demonstrated (Jaramillo et al., 2008, *Cancer Biol Ther*, 7, 557-568). To understand the inhibitory effect of GMI on EGF-promoted migration in A549 cells, the effects of GMI on EGF-induced cell motility and wound-healing assay were investigated.

Wound-Healing Assay

On wound-healing assay, the cancer cells were cultured onto 24-well plates and grown in medium containing 10% FBS to nearly confluent cell monolayer. A plastic pipette tip was used to draw a linear "wound" in the cell monolayer of each well. The monolayer was then washed twice with PBS to remove debris or detached cells, and GMI was added at different concentrations (0, 2, 4, and 8 mg/mL). PBS was added to the control well as the solvent control. After 24 h of incubation, the cells were washed twice with PBS, fixed with 95% alcohol, and stained with 10% Giemsa solution (Merck). The cells were photographed under a light microscope (magnification, X 200). The experiments were performed in triplicate. After incubation with 2-8 μg/ml of GMI for 24 h, the cells that migrated to the denuded zone were photographed. The results demonstrated that GMI dose-dependently suppresses A549 cell migration to the denuded zone (FIG. 1A). In contrast, the cells treated only with EGF showed acceleration of wound closure after treatment for 24 h (FIG. 1A). Cells co-treated with EGF and GMI demonstrated markedly decreased wound closure activity (FIG. 1A). On the other hand, AG1478, a positive control for EGF, was able to inhibit EGFR phosphorylation. AG1478 inhibition of EGF-induced migration was similar to that of GMI (FIG. 1B).

Cell Invasion Assay

Cell invasion assays were performed using modified Boyden chambers 6.5 mm in diameter, with 10 mm thick porous (8 µm) polycarbonate membrane separating the two chambers (Transwell; Costar, Cambridge, Mass.). The membrane of the upper chamber was coated with Matrigel (0.3 mg/mL; BD Biosciences Discovery Labware) for 3 hours. Condition medium was prepared from A549 cells which were pretreated with or without GMI, LY294002 (50 µM), or AG1478 (2 µM) for 8 h. To the medium of the bottom chamber was added 10% FBS-DMEM containing EGF (10 ng/ml) or condition medium. Cells were trypsinized, centrifuged, and resuspended at $4\times10^5$ cells/mL in 0.5% FBS-DMEM. After 24 h incubation, the cells on the upper well and the membranes coated with Matrigel were fixed with methanol, and stained with 20% Giemsa solution (Merck). The cells that were attached to the lower surface of the polycarbonate filter were counted under a light microscope (magnification, ×100). The experiments were performed in triplicate.

Figures 2, 2A:
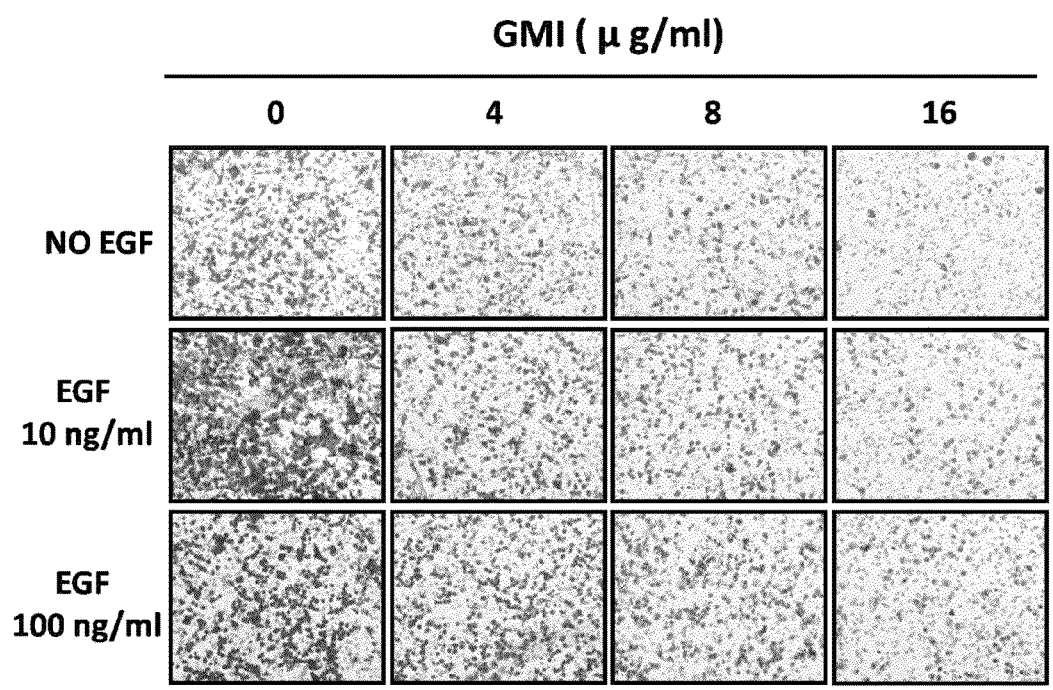
FIG. 2 shows the inhibition of GMI in EGF-induced invasion in A549 cells. A549 cells ($2 \times 10^4$ cells/well) were seeded onto the upper chamber of membrane and treated with different concentrations of GMI (4, 8, 16 µg/ml) for 2 hours. The bottom chamber was filled with DMEM supplemented with EGF 10 ng/ml or 100 ng/ml. After about 24 h, the invasive A549 cells passed through the membrane and were quantified by counting the cells that migrated onto the membrane. Cells were fixed, stained, and counted as described in the text. The data represent mean±SD.
Figures 2, 2B:
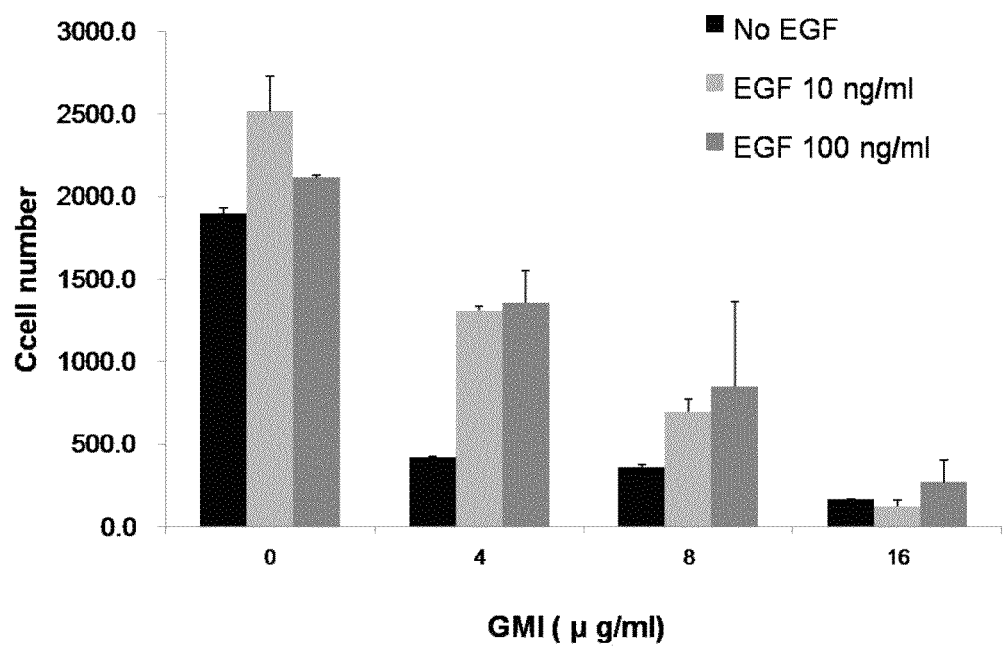

The invasive ability of tumor cells is one of the important characteristics of metastasis. Boyden chamber assay was modified to quantify the invasive potential of A549 cells. The results showed that GMI induced a dose-dependent decrease in invasion with increasing concentrations of GMI (FIG. 2A). At 4 µg/ml the invasion was reduced to 22% (invaded cell number decreased from 1895±37 to 419±6) and at 16 µg/ml the invasion was reduced to less than 9% (invaded cell number decreased from 1895±37 to 61±3). Subsequently, GMI induced a dose-dependent decrease in EGF-promoted invasion (FIG. 2A). At 4 µg/ml the invasion was reduced to 52% (invaded cell number decreased from 2515±212 to 1306±30) and at 16 µg/ml the invasion was reduced to less than 5% (invaded cell number decreased from 2515±212 to 121±39). The results demonstrated that GMI significantly inhibits EGF-promoted invasion of A549 cells.

Example 2

GMI Inhibits EGF-Induced Phosphorylation of EGFR, Akt and Stat3

Several studies have indicated that the transcription factors p38 MAPK, Stat3 and Akt are involved in cell metastasis activity in different cell types (Broadbelt et al., 2009, *Am J Physiol Renal Physiol*, 297, F114-124; Lee et al., 2008, *Toxicol Appl Pharmacol*, 226, 178-191; Shih et al., 2009, *Food Chem Toxicol*, 47, 1985-1995). Akt acts downstream of PI3K. It is a multifunctional regulator of cell survival, growth and invasion, and is phosphorylated within 10 min of EGF stimulation. These observations suggest that activation of Akt by EGF plays a role in the invasive activities of A549 cells.

Western Blotting

Total cell lysates were prepared in RIPA buffer (100 µl in 60 mm in dish). Fifty µg of lysate were loaded onto an 8% polyacrylamide gel and analyzed by SDS gel electrophoresis. After transfer to PVDF (Amersham), blots were blocked with 5% skim milk in TBS (10 mM Tris-CL pH7.5, 150 mM NaCl) containing 0.2% Tween-20. Blots were probed with antibodies (at their recommended dilutions) in 5% skim milk in TBS overnight at 4° C. Following detection with the appropriate horseradish-peroxidase conjugated secondary antibody (Cell Signaling), blots were developed by enhanced chemiluminescence according to the manufacturer's directions (Perkin Elmer Life Sciences). All experiments were performed in duplicate.

Actin Staining

Cells were washed twice with PBS and fixed in a 3.7% paraformaldehyde-PBS solution for 10 min at room temperature. After two additional washes with PBS, cells were permeabilized with a solution of 0.1% Triton X-100 in PBS for 3 to 5 min and washed again with PBS. Texas Red-X phalloidin (2 units/mL) and Alexa Fluor 488 DNase I conjugate (9 µg/mL) were used to localize filamentous actin (F-actin) and G-actin. Fluorescent dyes were diluted with blocking solution (1% bovine serum albumin and 0.025% saponin in PBS) and added to coverslips for 60 min at room temperature. After three washes with PBS, coverslips were mounted on a microscope slide with Prolong Gold antifade reagent with DAPI (Life Technologies). F-actin cytoskeleton imaging was performed with a confocal laser scanning microscope (ZEISS LSM510 BETA) at X400 magnification.

Figure 3:
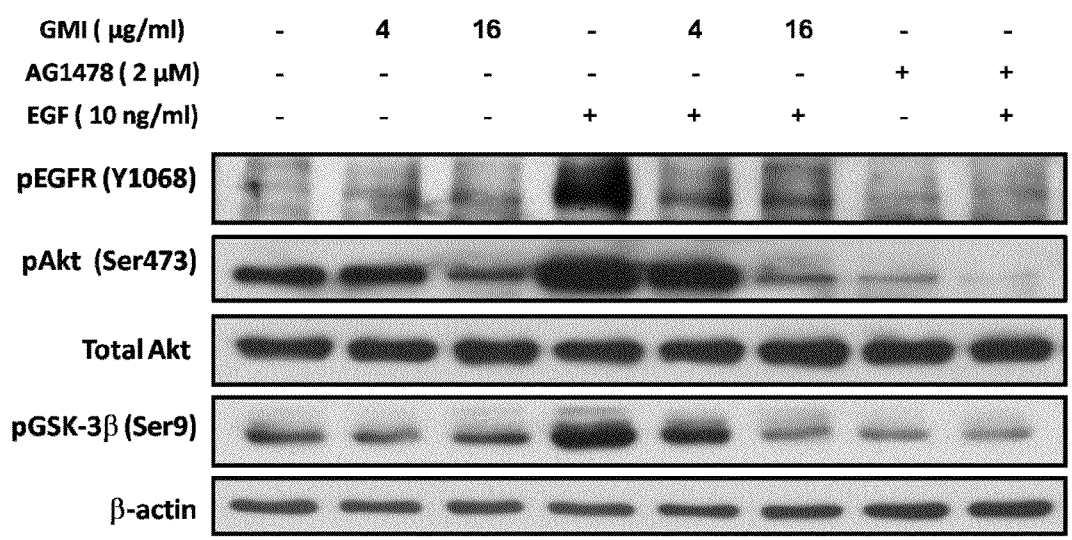
FIG. 3 shows the effects of GMI on signal transduction pathways in A549 cells. A549 cells ($5 \times 10^5$ cells/60 mm) were pretreated with various concentrations of GMI (4, 16 µg/ml) or AG1478 (EGFR inhibitors) for 8 hours prior to incubation for 10 minutes with EGF (as indicated). Cell lysates were subject to immunoblotting with phospho-specific EGFR (Y1068) (A and B), anti-phospho-AKT (A), anti-AKT (A), anti-phospho-GSK3β (A) or anti-phospho-STAT3 antibodies (B). Protein loading was determined by Western blotting against β-actin (A and B).
Figure 3:
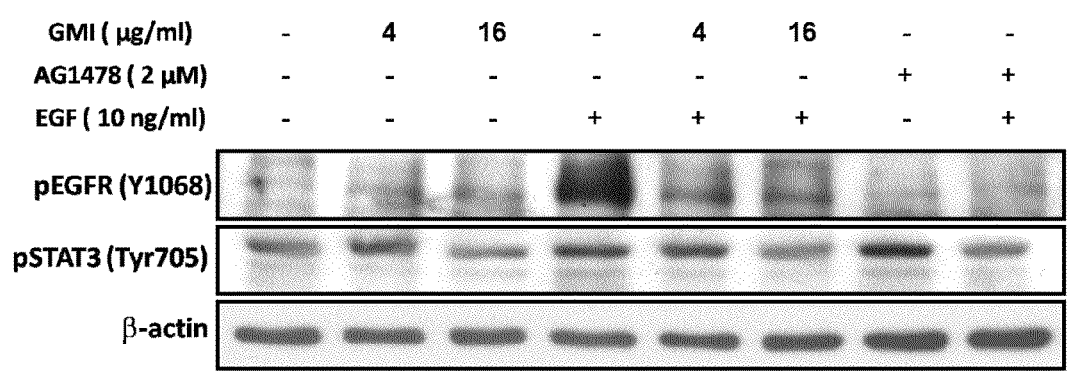
Figures 4, 4A:
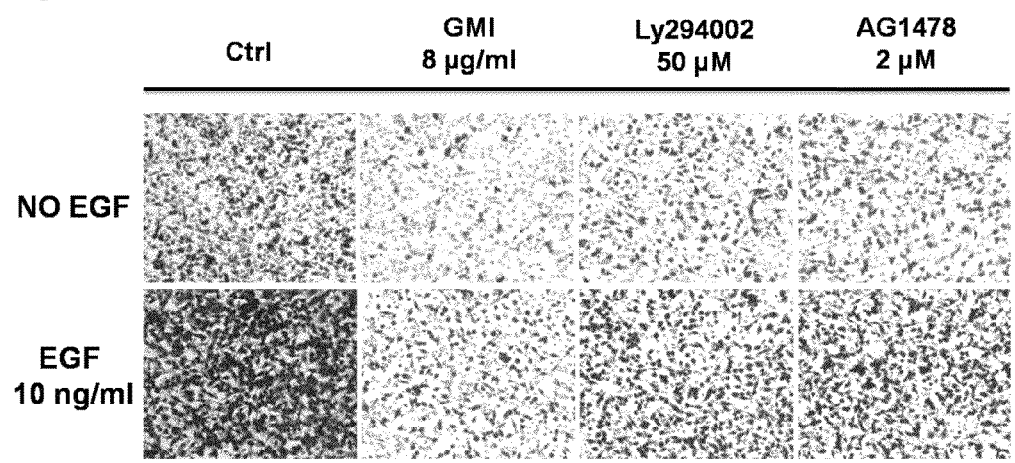
FIG. 4 shows the effect of GMI, PI3K inhibitor and EGFR inhibitor on EGF-induced invasion of A549 cells. EGF (10 ng/ml) was applied to the lower chamber as a chemoattractive agent. Serum-starved cells ($2 \times 10^4$ cells/well) were seeded onto the upper chamber consisting of 8-µm pore-size filters coated with Matrigel basement membrane matrix and then incubated with 8 µg/ml GMI, 50 µM Ly294002 (PI3K inhibitor) or 2 µM AG1478 (EGFR inhibitor) for 24 h. Cells that invaded the lower surface of the membranes were counted under a light microscope. The data are presented as mean±SD.
Figures 4, 4B:
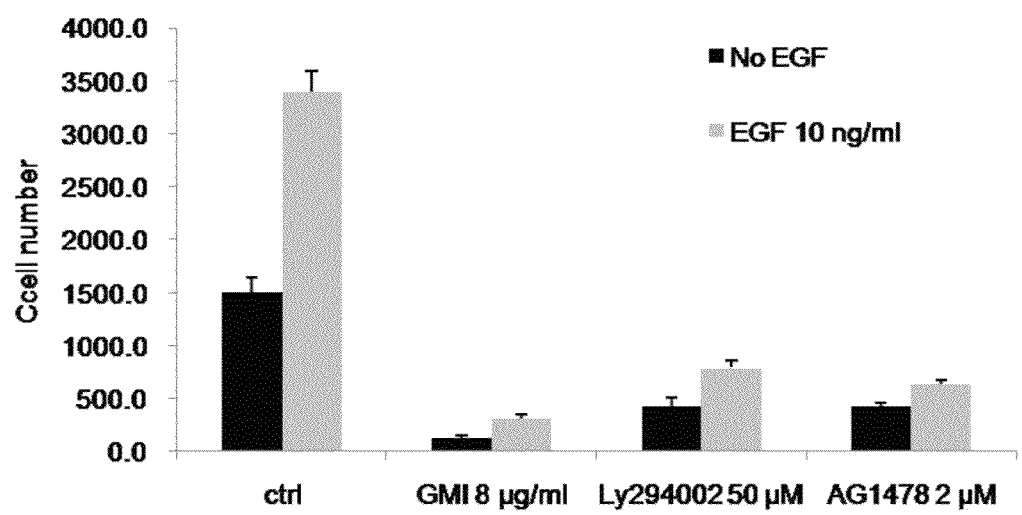

To assess whether GMI mediates and/or inhibits phosphorylation of Akt and Stat3, the invention investigated the effect of GMI on the phosphorylation status of Akt and Stat3 in A549 cells treated with various concentrations of GMI for 8 h. FIG. 3 show that GMI significantly inhibits EGF-induced activation of EGFR and Akt, whereas it has little effect on Stat3.

Example 3

GMI Inhibits Cdc42 Activity and Microfilament Depolymerization in A549 Cells

EGF induces cell proliferation and migration mainly through activation of its cell surface receptor EGFR. Rac1 activating signaling pathways are located downstream of EGFR (Binker et al., 2009, *Biochem Biophys Res Commun*, 379, 445-450).

Rac1 and Cdc42 Activity Assay

Active Rac1 and Cdc42 were determined by pull-down assay (Binker et al., 2009, *Biochem Biophys Res Commun*, 379, 445-450). Serum-starved A549 cells were or were not stimulated for 3 min with EGF and then collected in 800 µl of ice-cold lysis-buffer. Lysates were centrifuged to remove cellular debris. From each supernatant, 5 µl were taken out to measure protein content using Protein Assay Kit (Bio-Rad, Hercules, Calif.). Twenty µl were removed to determine total Rac1 in total lysate, and the remaining volume was used for the pull-down assay. Lysates containing equal amounts of proteins were then mixed with 15 µg of GST-PAK-PBD-beads (Pierce). Samples for total Rac1 and Cdc42 in total lysate and the pelleted beads were diluted in Laemmli sample-buffer and boiled. The proteins were separated using SDS-PAGE (12% gel). After transfer to nitrocellulose membranes (Bio-Rad), blots were blocked with bovine serum albumin, followed by incubation with Rac1 antibody overnight. Binding of the antibody was visualized using peroxidase-coupled anti-mouse antibody and chemiluminescence method (Perkin Elmer Life Sciences). Equal loading was verified by reprobing membranes corresponding to total lysate with anti-β-actin antibody (not shown).

Figure 5:
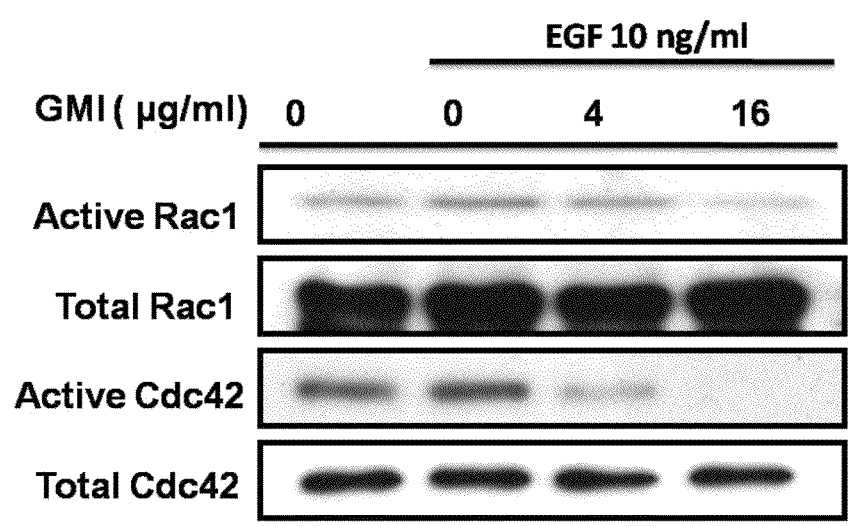
FIG. 5 shows the inhibition of GMI in EGF-induced activation of Cdc42. A549 cells were seeded onto 100 mm plates and cultured to around 80% confluence. The cells were then treated with various doses of GMI (4, 16 µg/ml). GMI inhibits Cdc42 activation but has little effect on Rac1. A549 cells were pretreated with various concentrations of GMI for 24 h before being stimulated with 10 ng/mL EGF for 3 min. After that, cells were washed with cold PBS and lysated on the dish in RIPA buffer. Active GTP-bound Rac1 or Cdc42 was pulled down using the GST-PBD fusion protein of PAK1 immobilized on glutathione beads and active Rac1 and Cdc42 were detected with anti-Rac1 and anti-Cdc42 antibodies.

To determine the relationship between the anti-invading effect of GMI and Rac1/Cdc42 signaling pathway, the effect of GMI on Rac1 activity was evaluated. As shown in FIG. 5

(Lanes 1 and 2), Rac1 and Cdc42 activities are induced by 10 ng/ml EGF for 3 min. In contrast, GMI reduced EGF-promoted Cdc42 activity in a dose-dependent manner, with little reduction in Rac1 activity in A549 cells (FIG. 5, lane 2 to lane 4). However, Rac1 activity correlated directly with cell mobility.

Figure 6:
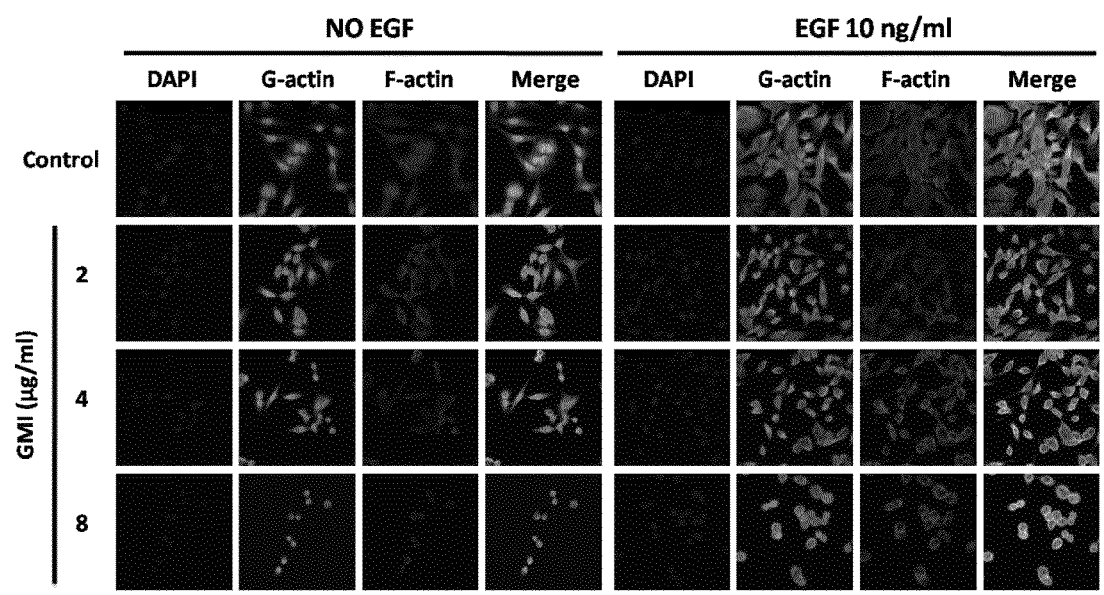
FIG. 6 shows the effects of GMI on EGF-induced F-actin/G-actin ratio and filopodia formation. A549 cells ($1 \times 10^4$ cells/well) were seeded onto 24 wells with coverslip. A549 cells were pretreated with various concentrations of GMI (2, 4, 8 µg/ml) for 1 h before being stimulated with 10 ng/mL EGF for 23 h. A549 cells treated with or without EGF were stained with Texas Red®-X phalloidin and Alexa Fluor 488 DNase I conjugate to detect F-actin (red) and G-actin (green). F-actin labeling with Texas Red®-X phalloidin revealed that A549 cells exhibited numerous filopodia, whereas GMI-treated cells exhibited fewer filopodia fibers.

Given that reorganization of the actin cytoskeleton is a critical determinant of cellular invasion, the invention next analyzed the G-actin and F-actin cytoskeletal architecture in GMI-treated cells with EGF (Denys et al., 2008, *Cancer Lett*, 266, 263-274). EGF plays an important role in the progression of breast carcinomas, and as previously shown (Lu et al., 2003, *Cancer Cell*, 4, 499-515). EGF at 10 ng/ml over 72 h can induce EMT in A431 cells. In this study, as shown in FIG. 6, EGF induced F-actin fibers (red) and increased G-actin fibers (green). Lamellipodia formations were observed in A549 cells with EGF for 24 h. GMI abrogated elongation and polymerization of F-actin and G-actin in A549 cells treated with EGF or GMI alone. Focal contact size was also reduced by GMI in a dose-dependent manner and with combined treatment.

Example 4

Effect of Cisplatin and GMI Co-Treatment on CaLu-1 or A549 Cell Viability

CaLu-1 cells were co-treated with various concentrations of cisplatin (0, 2.5, 5, 10, 20 μM) and GMI from *Ganoderma microsporum* (0, 4, 8 and 16 μg/mL) for 48 h followed by MTT assay to estimate cell viability. The synergistic effect was determined after co-treated Cisplatin and GMI.

MTT assay was used to determine the effect of GMI and cisplatin on the proliferation of Calu-1 cells. In metabolically active cells, MTT (Thiazolyl Blue Tetrazolium Bromide) (SIGMA) was reduced by dehydrogenase enzyme into an formazan product. Absorbance was measured directly at 570 nm from 96-well assay plates after adding 100 μl DMSO. The quantity of formazan was considered to be directly proportional to the number of viable cells in the culture.

Briefly, the cells ($5 \times 10^3$) were incubated on 96-well plates containing 200 μl of growth medium. After 24 h incubation, the medium was carefully removed and 100 μl of fresh medium containing various concentrations of GMI and cisplatin were added to the wells. The cells were treated with GMI and cisplatin continuously for 48 h with 0, 4, 8, 16 μg/ml for GMI and with 0, 2.5, 5 and 10 μM for cisplatin. At the end of this process, 100 μl/well of 0.5 mg/ml MTT solution was added and wells were incubated for 3 h, 37° C., in a humidified incubator. The supernatant was aspired and 100 μl DMSO was added therein to solve the formazan The absorbance was analyzed on a VERSAmax microplate reader at 570 nm Absorbance values were presented as the mean±SE of 3 replicates for each treatment. Cells in controls and compound controls were included. Absorbance of untreated cells was considered 100%.

Figure 7:
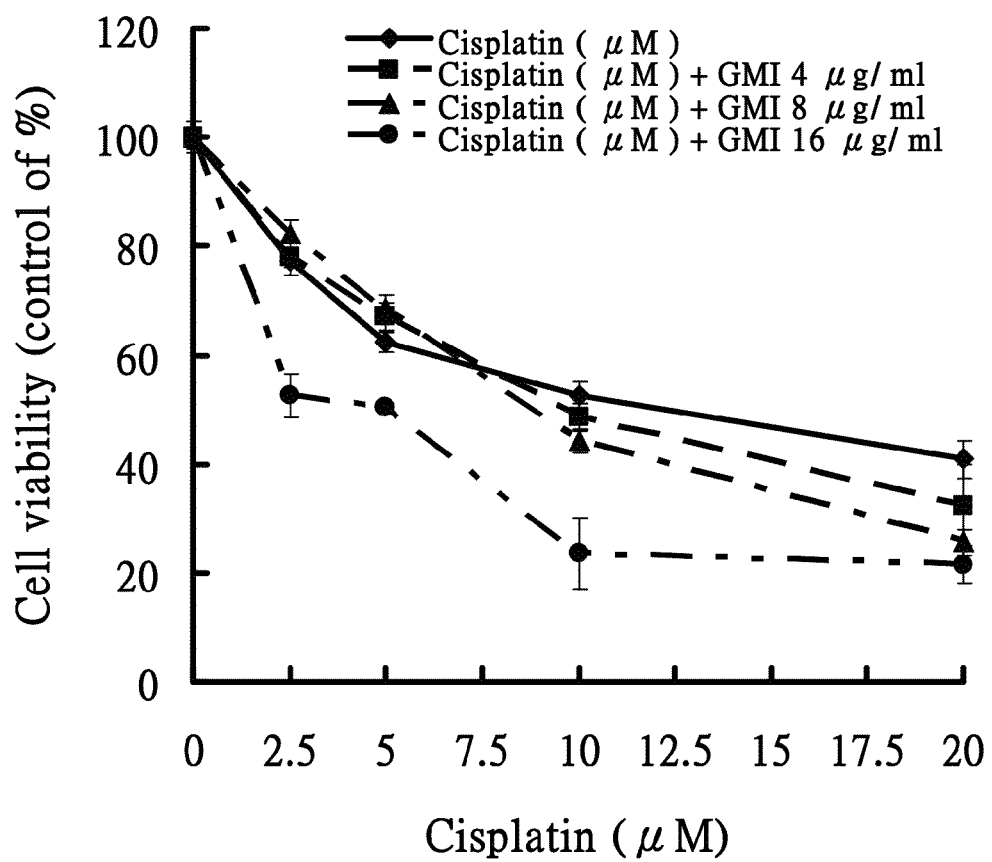
FIG. 7 shows the effect of cisplain and GMI co-treatment on CaLu-1 cells viability.

As shown in FIG. 7, the combination of GMI and cisplatin exhibits a synergistic effect and the amount of cisplatin can be largely reduced when it is combinatorially used with GMI. For example, 2.5 μM cisplatin in combination with 16 μg/ml GMI can achieve about 50% cell viability, whereas cisplatin alone needs about 10 μM to achieve the same viability.

What is claimed is:

1. A method for inhibiting EGF receptor activity in lung cancer cells comprising contacting an EGF receptor with a pharmaceutical composition wherein the pharmaceutical composition comprises GMI or a recombinant thereof and an anti-cancer agent, wherein the GMI and the anti-cancer agent are in a synergistic amount in inhibiting EGF receptor in lung cancer cells, and wherein GMI has the amino acid sequences of: (1)-Leu-Ala-Trp-Asn-Val-Lys-(LAWNVK; SEQ ID NO:1) and (2)-Asp-Leu-Gly-Val-Arg-Pro-Ser-Tyr-Ala-Val-(DLGVRPSYAV; SEQ ID NO:2) or the amino acid sequence of MSDTALIFTLAWNVKQLAFDYTPNWGR-GRPSSFIDTVTFPTVLTDKAYTYRVVVSGKD LGVRPSYAVESDGSQKINFLEYNSGY-GIADTNTIQVYVIDPDTGNNFIVAQWN (SEQ ID NO:3), and wherein the anti-cancer agent is cisplatin.

2. A method for treating lung cancer and/or inhibiting invasion and metastasis of lung cancer cells comprising administering an effective amount of a pharmaceutical composition to a subject in need of such treatment; wherein the pharmaceutical composition comprises GMI or a recombinant thereof and an anti-cancer agent, wherein the GMI and the anti-cancer agent are in a synergistic amount in treating lung cancer and/or inhibiting invasion and metastasis of lung cancer cells, and wherein GMI has the amino acid sequences of: (1)-Leu-Ala-Trp-Asn-Val-Lys-(LAWNVK; SEQ ID NO:1) and (2)-Asp-Leu-Gly-Val-Arg-Pro-Ser-Tyr-Ala-Val-(DLGVRPSYAV; SEQ ID NO:2) or the amino acid sequence of: MSDTALIFTLAWNVKQLAFDYTPNWGR-GRPSSFIDTVTFPTVLTDKAYTYRVVVSG KDLGVRPSYAVESDGSQKINFLEYNSGY-GIADTNTIQVYVIDPDTGNNFIVAQWN (SEQ ID NO:3), and wherein the anti-cancer agent is cisplatin.

3. The method according to claim 2, wherein the invasion and metastasis of the lung cancer cells is epidermal growth factor mediated migration and invasion of the lung cancer cells.

4. The method according to claim 2, wherein the lung cancer is non-small lung carcinoma (NSCLC).

5. The method according to claim 2, wherein the pharmaceutical composition is administered parenterally.

6. The method according to claim 2, wherein the pharmaceutical composition is administered orally or rectally.

7. The method according to claim 2, wherein the pharmaceutical composition is used in cancer chemoprevention.

8. The method according to claim 2, wherein the pharmaceutical composition is administered in combination with radiotherapy and chemotherapy.

9. The method of claim 2, wherein the GMI or the recombinant thereof and the anti-cancer agent are administered simultaneously, sequentially or separately.

10. A pharmaceutical composition, comprising GMI or a recombinant thereof and an anti-cancer agent, wherein the GMI and the anti-cancer agent are in a synergistic amount in inhibiting EGF receptor and/or treating lung cancer and/or inhibiting invasion and metastasis of lung cancer cells, and wherein GMI has the amino acid sequences of: (1)-Leu-Ala-Trp-Asn-Val-Lys-(LAWNVK; SEQ ID NO:1) and (2)-Asp-Leu-Gly-Val-Arg-Pro-Ser-Tyr-Ala-Val-(DLGVRPSYAV; SEQ ID NO:2) or the amino acid sequence of MSDTALIFT-LAWNVKQLAFDYTPNWGRGRPSS-FIDTVTFPTVLTDKAYTYRVVVSGKD LGVRPSYAVESDGSQKINFLEYNSGY-GIADTNTIQVYVIDPDTGNNFIVAQWN (SEQ ID NO:3), and wherein the anti-cancer agent is cisplatin.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Ganoderma microsporum

<400> SEQUENCE: 1

Leu Ala Trp Asn Val Lys
1               5

<210> SEQ ID NO 2
<211> LENGTH: 10
<212> TYPE: PRT
<213> ORGANISM: Ganoderma microsporum

<400> SEQUENCE: 2

Asp Leu Gly Val Arg Pro Ser Tyr Ala Val
1               5                   10

<210> SEQ ID NO 3
<211> LENGTH: 111
<212> TYPE: PRT
<213> ORGANISM: Ganoderma microsporum

<400> SEQUENCE: 3

Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
            20                  25                  30
```

```
Phe Ile Asp Thr Val Thr Phe Pro Thr Val Leu Thr Asp Lys Ala Tyr
        35                  40                  45

Thr Tyr Arg Val Val Val Ser Gly Lys Asp Leu Gly Val Arg Pro Ser
    50              55              60

Tyr Ala Val Glu Ser Asp Gly Ser Gln Lys Ile Asn Phe Leu Glu Tyr
65              70              75                          80

Asn Ser Gly Tyr Gly Ile Ala Asp Thr Asn Thr Ile Gln Val Tyr Val
            85              90                          95

Ile Asp Pro Asp Thr Gly Asn Asn Phe Ile Val Ala Gln Trp Asn
            100             105                 110
```